United States Patent
Prince et al.

(10) Patent No.: US 11,832,998 B2
(45) Date of Patent: Dec. 5, 2023

(54) PENICILLIN ALLERGY TESTING KIT

(71) Applicants: Ty L. Prince, Knoxville, TN (US);
Herman J. Novak, Maryville, TN (US)

(72) Inventors: Ty L. Prince, Knoxville, TN (US);
Herman J. Novak, Maryville, TN (US)

( * ) Notice: Subject to any disclaimer, the term of this patent is extended or adjusted under 35 U.S.C. 154(b) by 0 days.

(21) Appl. No.: 18/116,340

(22) Filed: Mar. 2, 2023

(65) Prior Publication Data
US 2023/0200933 A1    Jun. 29, 2023

Related U.S. Application Data

(63) Continuation-in-part of application No. 17/658,270, filed on Apr. 7, 2022, and a continuation-in-part of application No. 17/468,132, filed on Sep. 7, 2021, now Pat. No. 11,369,782, and a continuation-in-part of application No. 17/402,413, filed on Aug. 13, 2021, now Pat. No. 11,517,249.

(51) Int. Cl.
*A61B 90/94* (2016.01)
*A61B 50/33* (2016.01)
*A61B 5/00* (2006.01)

(52) U.S. Cl.
CPC ............ *A61B 90/94* (2016.02); *A61B 5/0022* (2013.01); *A61B 5/411* (2013.01); *A61B 5/7264* (2013.01); *A61B 50/33* (2016.02)

(58) Field of Classification Search
CPC ....... A61B 90/94; A61B 50/33; A61B 5/0022; A61B 5/411; A61B 5/7264
USPC .......................................................... 600/556
See application file for complete search history.

(56) References Cited

U.S. PATENT DOCUMENTS

| | | | |
|---|---|---|---|
| 2005/0101844 A1* | 5/2005 | Duckert | G16H 40/67 600/300 |
| 2010/0012537 A1* | 1/2010 | Farrar | B65D 77/046 206/364 |
| 2016/0228046 A1* | 8/2016 | Smollar | A61B 50/33 |
| 2017/0027494 A1* | 2/2017 | Strader | A61B 5/411 |

* cited by examiner

*Primary Examiner* — Alex M Valvis
*Assistant Examiner* — Chanel J Jhin
(74) *Attorney, Agent, or Firm* — Gerald R. Black, Esq.

(57) ABSTRACT

The kit evaluates the patient's skin for penicillin sensitivity. The kit comprises a container, a multi-site skin test system, five preloaded syringes, and a tattoo-type label that is transferable onto the patient's skin. A multi-site skin test applicator is cooperatively engageable with four reservoirs in a fluid tray. The applicator pierces the patient's skin as trace amounts of the allergy test fluids are simultaneously administered. The tattoo-type label is transferable onto the skin of the patient and includes a QR Code. The QR Code includes machine-readable linkage to artificial intelligence for assisting a doctor in interpreting patient test results. The doctor reviews the artificial intelligence analysis and decides either to accept the analysis or modify it. The doctor may also decide to verify negative results with a subcutaneous skin test. The five syringes are preloaded with saline, two syringes are preloaded with Pre-Pen, and two syringes are preloaded with Pen-G.

20 Claims, 14 Drawing Sheets

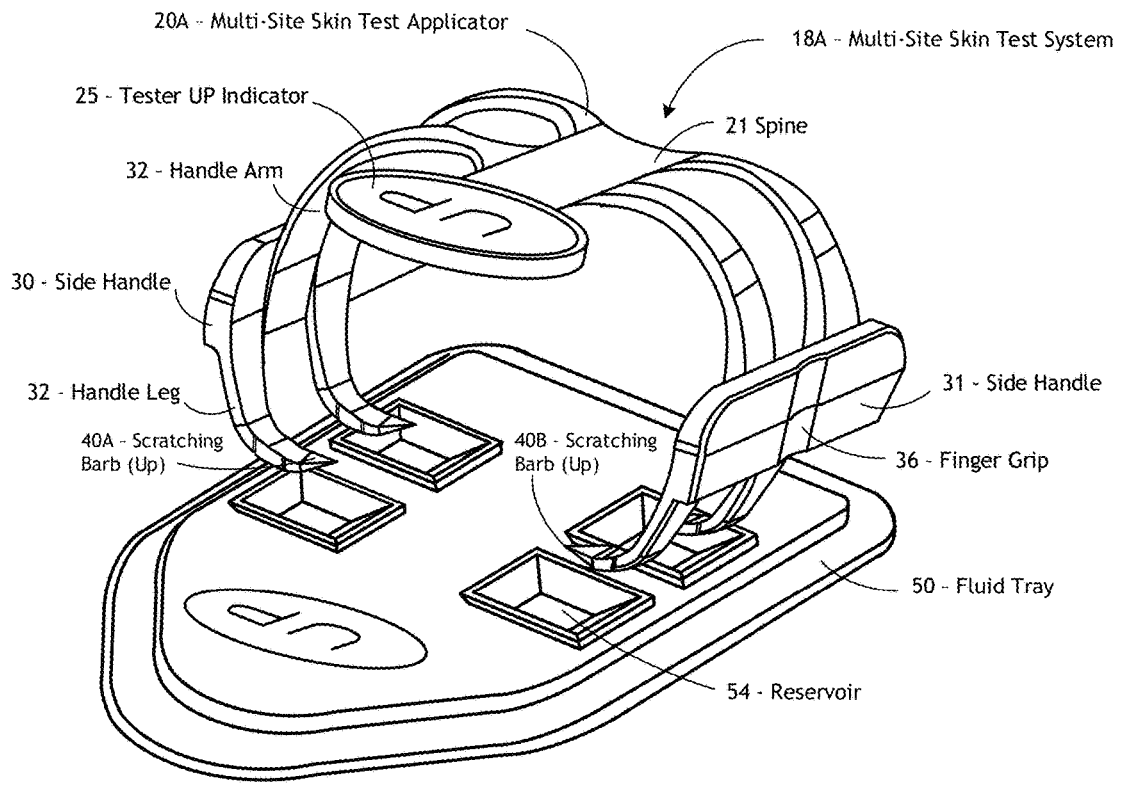
Fig. 8
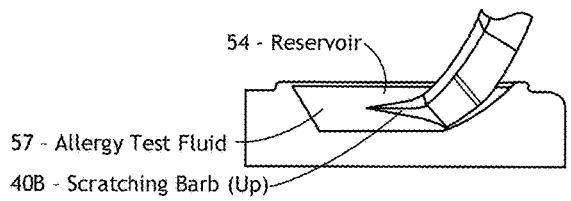
DETAIL "A"
Allergy Fluid Loading Position

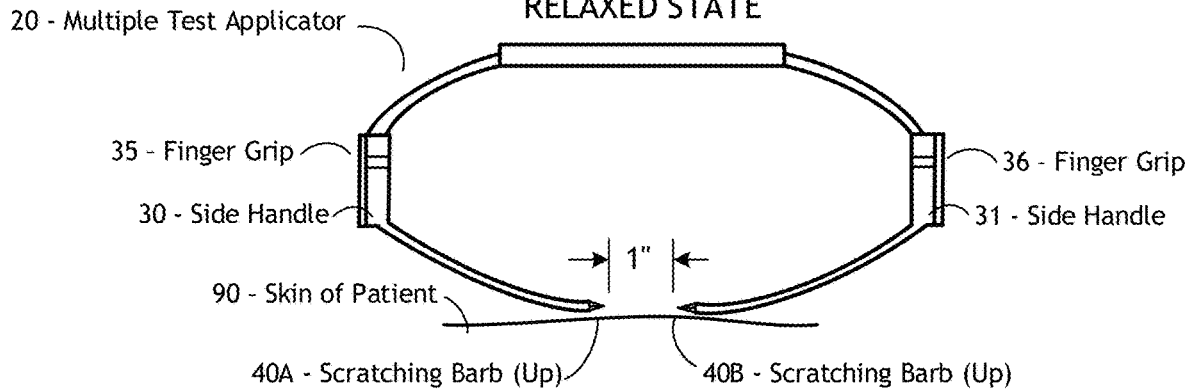
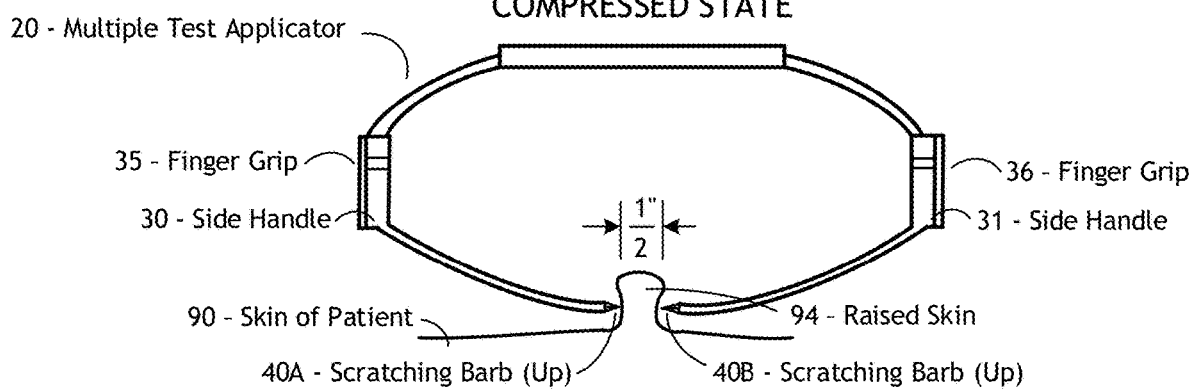
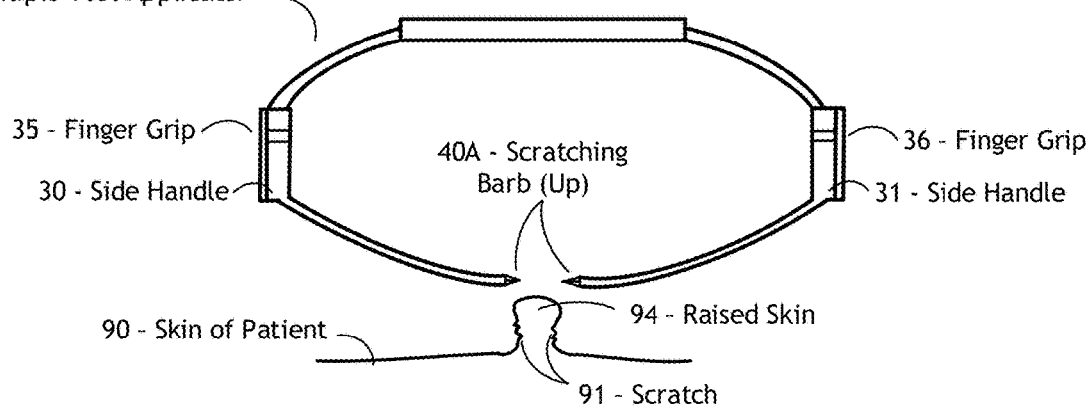

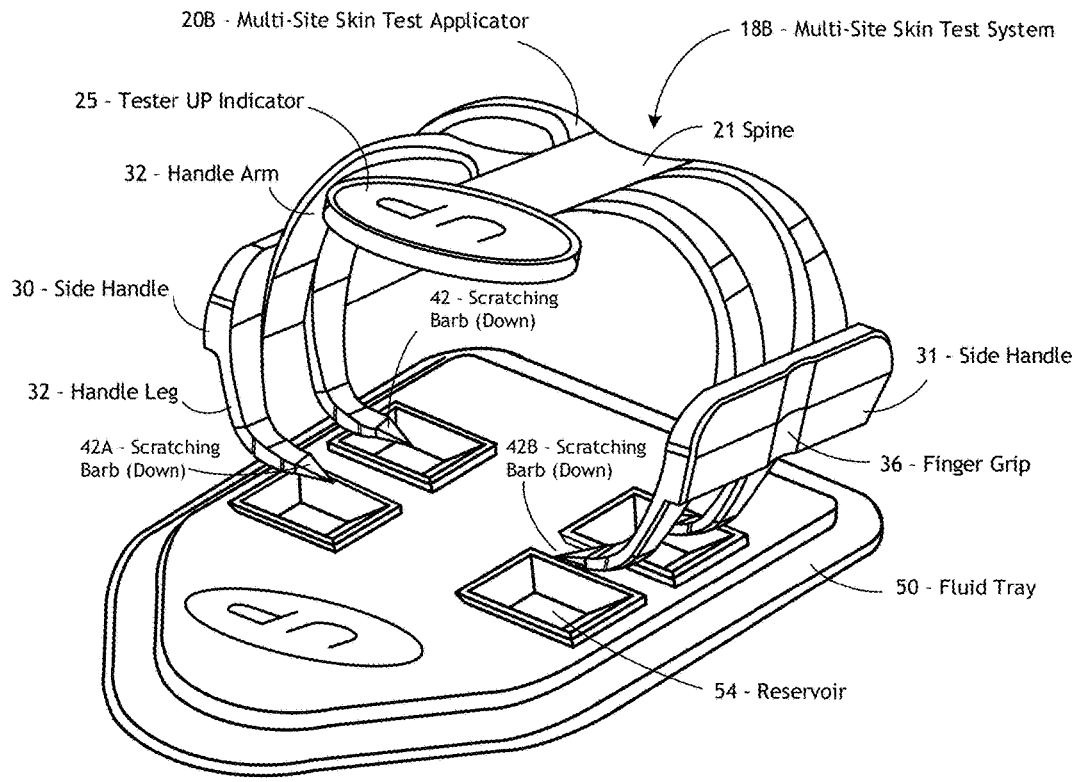
Fig. 10
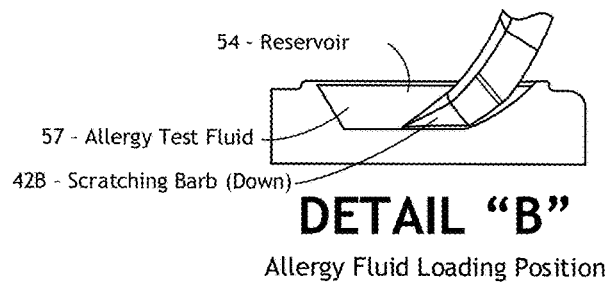
DETAIL "B"
Allergy Fluid Loading Position

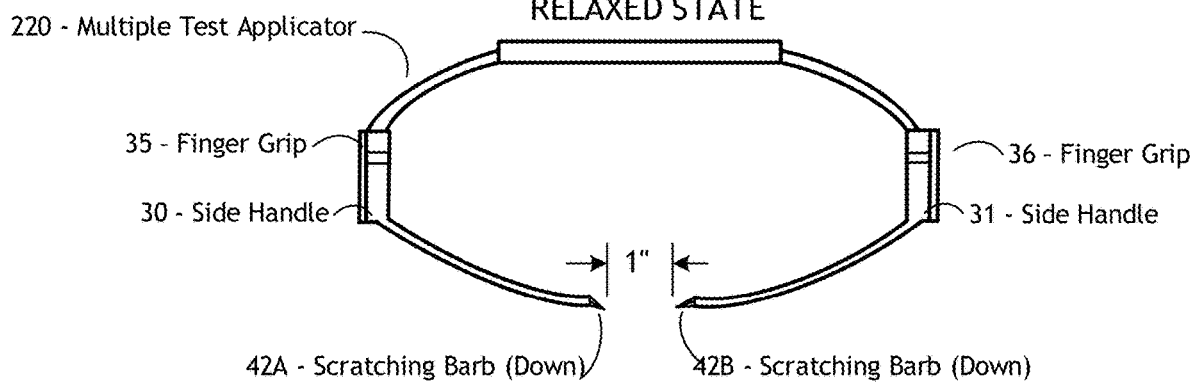
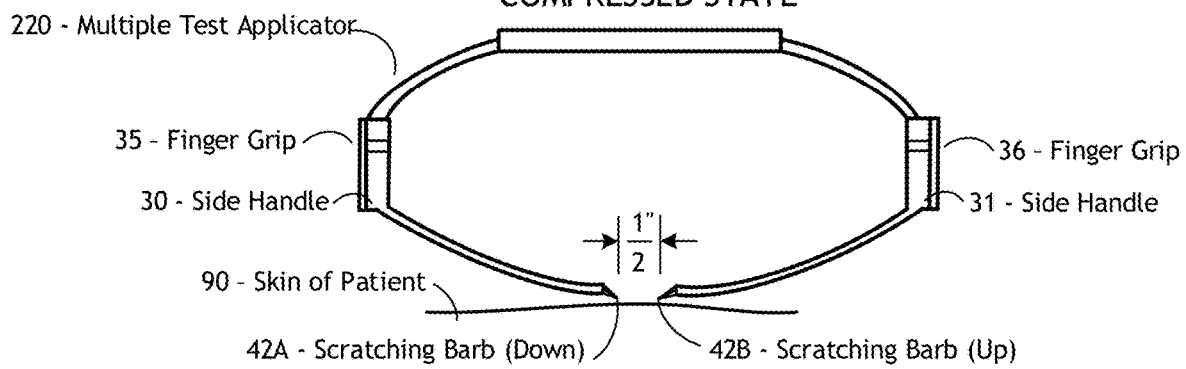
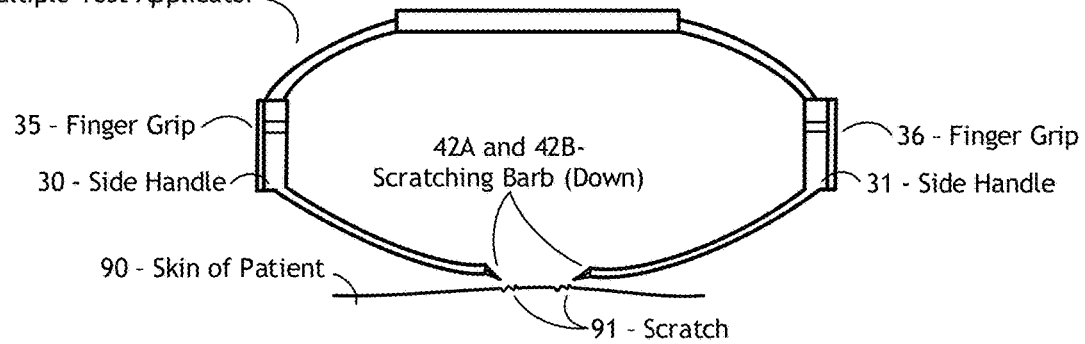

SHIPPING POSITION

INSERTION POSITION

DISPOSAL POSITION

PENICILLIN ALLERGY TESTING KIT

CROSS-REFERENCE TO RELATED APPLICATIONS

This Application is a continuation-in-part to and claims priority to U.S. patent application Ser. No. 17/658,270 entitled "Penicillin Allergy Test Kit" (Prince and Novak), filed on Apr. 7, 2022; U.S. patent application Ser. No. 17/468,132 entitled "Methods for Administering Multiple Allergens" (Prince), filed on Oct. 28, 2021; U.S. patent application Ser. No. 17/402,413 entitled "Multiple Allergen Test Applicator" (Prince), filed on Aug. 13, 2021; U.S. Provisional Application No. 63/177,515 entitled "Single and Multiple Allergen Testing System" (Prince), filed on Apr. 21, 2021; U.S. Provisional Application No. 63/171,995, entitled "Penicillin Allergy Test Kit" (Prince and Novak) filed on Apr. 7, 2021; and U.S. Provisional Application No. 63/106,793 entitled "Single and Multiple Allergen Skin Testing System" (Prince), filed on Oct. 28, 2020.

FIELD OF THE INVENTION

The present invention relates to diagnostic kits, and more particularly to diagnostic kits for determining hypersensitivity on the skin of a patient to penicillin.

BACKGROUND OF THE INVENTION

Since the 1940s, penicillin has been the go-to drug to clear up infections caused by bacteria. Penicillin can treat many serious conditions. For some, penicillin may be the only effective option available. Penicillin has saved many lives over the years. Penicillin is one of the few drugs for which standardized allergy skin tests are available.

However, estimates show that about 10% of all people report having an allergic reaction to penicillin at some time in their lives. A patient's immune system is supposed to fight off the bacteria that make the patient ill. But sometimes the body fights the medicine itself. The immune system reacts to penicillin as an invader and attacks it.

The primary references in the prior art for determining a penicillin hypersensitivity are:

U.S. patent application Ser. No. 15/975,070 (Mendelson; et al.) discloses kits and methods to detect penicillin allergy. The kits evaluate on the skin of a patient the sensitivity to penicillin, comprising a first vial containing a major determinant mixture, the major determinant mixture comprising benzylpenicilloyl polylysine; a second vial containing lyophilized minor determinant mixture, the minor determinant mixture comprising a lyophilized mixture of neutralized (1) penicillin G potassium; (2) penicilloic acid; and (3) penilloic acid; a third vial containing amoxicillin sodium; and instructions for carrying out a method to evaluate on the skin of a patient the sensitivity to penicillin. The kit also is directed to a method to rule out penicillin allergy. This Patent Application was assigned to Allerquest, LLC.

U.S. Pat. No. 3,867,365 (Stahlman; et al.) discloses penicilloyl-polylysine conjugates having dextro-rotary optical activity, and methods for their preparation and use. The stereo-isomeric penicilloyl-polylysine conjugates have high optical dextro-rotations are useful for eliciting cutaneous responses in persons with penicillin hypersensitivity. The process for manufacturing the above-identified stereospecific conjugates reacts penicillin with neutralized polylysine hydrochloride in a non-aqueous polar solvent such as dimethyl sulfoxide. This Patent is Pre-Pen®, which is the only FDA approved skin test for the diagnosis of penicillin allergy. This Patent was assigned to Allerquest, LLC.

U.S. Pat. No. 4,183,819 (Levine) discloses method for testing to predict or diagnose allergy to penicillin, and compounds and compositions for use in such tests. The invention relates to the testing of humans or other animals, for allergic reaction or hypersensitivity to penicillin. The tests can be used both to predict and to diagnose allergy. The invention comprises new penicilloyl-polylysine preparations, new materials for use in minor determinant mixture compositions and novel test methods employing such materials. The new penicilloyl-polylysine preparations comprise homogeneous, high purity, maximally coupled, .alpha.-diastereoisomeric, penicilloyl conjugates of low molecular weight penicilloyl-polylysines.

U.S. Pat. No. 4,316,882 (Levine) discloses compositions for testing to predict or diagnose allergy to penicillin. In view of the possibly catastrophic consequences of observing a negative response in a patient who is allergic to penicillin, it is critical that the most sensitive and highly reliable allergy tests be made clinically available. Further, the use of the most sensitive test is of importance when doing prick or scratch tests. These are much more convenient but less sensitive than intradermal tests. More sensitive test materials permit the use of a prick test. Accordingly, the principal objective of my invention is to provide a more sensitive and reproducible skin test for penicillin allergy using improved minor determinant mixture preparations. Another purpose is to provide novel minor determinant mixture compounds and compositions, including storage-stable minor determinant mixture materials, for use in skin testing for prediction or diagnosis of penicillin allergic reaction or hypersensitivity. The invention relates to the testing of humans or other animals, such as horses, cattle, or dogs, for allergic reaction or hypersensitivity to penicillin. The tests can be used both to predict and to diagnose allergy. The invention comprises new materials for use in minor determinant mixture compositions and lyophilized, storage-stable minor determinant mixture compositions and novel test methods employing such materials. The new minor determinant mixture materials are N-penicilloyl amines of an aliphatic amine or .alpha.-aminoacid.

Many people who have a reaction to penicillin can take penicillin again later in life. Sensitivity to the drug may decrease with time. An accurate diagnosis of a penicillin allergy is needed to ensure the best treatment options going forward.

The job of trying to match the right antibiotic to the right ailment is much tougher if a patient has a penicillin allergy. A misdiagnosed penicillin allergy may result in the use of a less-effective or more-expensive antibiotic.

Penicillin skin testing is grossly underused, due in large measure to the lack of a commercially available skin test kits that provide a comprehensive diagnosis. What is needed is a comprehensive, standardized single-patient test kit to screen patients to identify those that have a sensitivity to penicillin.

The objective of the present invention is to provide a safe and reliable test for penicillin sensitivity in less time and for less cost than traditional methods. A safe and reliable test for penicillin sensitivity is needed that is cost-effective and causes minimal discomfort to the patient, while improving testing accuracy.

SUMMARY OF THE INVENTION

The penicillin allergy test kit of the present invention addresses these needs and these objectives.

As used herein, a "scratch" is defined as an arcuate line, a straight line, or a jagged mark produced on the skin of a patient by scraping or abrading with a rough surface.

As used herein a "puncture" is a sharply pointed object that generates a hole, penetrating the skin of the patient.

As used herein, "piercing" includes a type of device that either punctures the skin of the patient or scratches the skin of the patient.

As used herein, "machine-readable code" refers to different types and shapes, that contain information about the item to which the codes are attached. With the passage of time, these codes have been advanced from one-dimensional codes to two-dimensional and now come in squares or circles with three-dimensional and other types of codes are in use since long.

The test kit of the present invention evaluates the skin of a patient for penicillin sensitivity. The kit comprises a container, a multi-site skin test applicator and fluid tray, five preloaded syringes, and a tattoo-type label that is transferable onto the skin of the patient.

The multi-site skin test applicator is cooperatively engageable with four reservoirs in the fluid tray. The applicator pierces the skin of the patient as trace amounts of the allergy test fluids are simultaneously administered into multiple test sites on the skin of the patient.

The multi-site skin test applicator is preferably made of a compressible material, the multi-site skin test applicator having a relaxed state and a compressed state. The multi-site skin test applicator is in the relaxed state while the barb loading of the allergy test fluids when the multi-site skin test applicator is cooperatively engaged with the fluid tray. The multi-site skin test applicator preferably includes a first finger grip disposed on a first side frame and a second finger grip disposed on a second side frame.

The tattoo-type label includes a machine-readable code and is transferable onto the skin of the patient. The machine-readable code includes linkage to artificial intelligence for assisting a doctor in interpreting the results of the patient's skin test. The machine-readable code is preferably a QR Code. The QR Code on the container links the kit to instructions and a training video for a medical professional. The doctor reviews the artificial intelligence analysis for this patient and decides either to accept the analysis or modify it. The doctor may also decide to verify negative results with a subcutaneous skin test, whereby a needle is inserted into the skin of the patient.

The five preloaded syringes are each identified as to content and enable the doctor to readily verify negative results with additional subcutaneous skin tests.

One syringe is preloaded with saline, two syringes are preloaded with Pre-Pen, and two syringes are preloaded with Pen-G.

The multi-site skin test applicator and the fluid tray, and the five preloaded syringes are stored in the container for shipping and for disposal after use.

The kit also includes a tattoo-type skin transfer label that can be placed on the skin of a patient, perhaps the upper arm for subcutaneous testing. The label includes a QR Code. The kit may also include a tattoo-type skin transfer label that can be placed onto a forearm of the patient being tested. The QR Code provides linkage to artificial intelligence for assisting the doctor in interpreting patient test results. The artificial intelligence improves interpreting test results continually as additional patients are evaluated and added to the system.

The container is preferably made of a material that prevents the scratching barbs and the syringe needles from penetrating through the surface of the container. The container is preferably made of a material that absorbs any liquid. When the container is closed, the container locks.

Each syringe preferably includes a safety syringe cover and a needle hub. The needle is secured within the needle hub. The unused needle is preferably locked in a first position and secured within the safety cover of the safety syringe during shipping. The needle is secured within the needle hub. The needle is preferably locked in a second position and secured within the safety cover of the safety syringe during insertion. The used needle is preferably locked in a third position and secured by the safety syringe awaiting disposal.

The penicillin allergy test kit of the present invention is compatible with an APP on a smart phone, a tablet or other electronic device where the APP has been installed.

As used herein, "Pre-Pen" (benzylpenicilloyl polylysine injection USP) is a registered trademark of Allerquest, LLC. Pre-Pen is the only FDA approved skin test for the diagnosis of penicillin allergy. Penicillin allergy testing can be performed safely on hospitalized patients and suggests improved outcomes, less vancomycin use, and potential cost savings. Penicillin skin testing is the most rapid, sensitive, and cost-effective modality for evaluating patients with immediate allergic reactions to penicillin. The Pre-Pen process is described in U.S. Pat. No. 3,867,365 (Stahlman; et al.).

"Pen-G" is a suspension of penicillin G procaine in 100-ml and 250-ml multiple dose vials. Each ml is designed to provide 300,000 units of penicillin G, as procaine in a stable suspension. Penicillin G procaine is an antibacterial agent which has activity against a variety of pathogenic organisms, mainly in the Gram-positive category.

Still other objectives of the penicillin allergy test kit of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIG. 8 depicts an assembly view of a first preferred embodiment of a multi-site skin-test applicator and fluid tray for use in the allergy test kit of the present invention, comprising a first preferred embodiment of the multi-site skin-test applicator having four applicators cooperatively engaged with a fluid tray, the multi-site skin-test applicator having four scratching barbs that simultaneously scratch the skin of the patient as trace amounts of allergy test fluids are inserted into the skin of the patient, the multi-site skin-test applicator being disposed on the fluid tray; and DETAIL "A" depicting an exploded side view of the scratching barb positioned in a reservoir of the fluid tray during the loading of allergy test fluids, the reservoir being partially filled with an allergy test fluid.

FIG. 9A is a front view of the multi-site skin-test applicator of FIG. 8, the multi-site skin-test applicator being in an expanded position, the pair of opposing scratching barbs resting upon the skin of a patient.

FIG. 9B is a front view of the multi-site skin-test applicator of FIG. 9A, the multi-site skin-test applicator now being in a compressed position, the pair of opposed scratching barbs resting upon the skin of a patient with each of the scratching barbs disposed at two test sites of a patient, with the skin having been lifted upwards between the pair of opposed scratching barbs.

FIG. 9C is a front view of the multi-site skin-test applicator of FIG. 9B, the multi-site skin-test applicator still being in a compressed position, the pair of opposed scratching barbs now being raised from the skin of the patient with scratches now appearing on each side of the raised skin of the patient.

FIG. 10 depicts an assembly view of a second preferred embodiment of a multi-site skin-test applicator and fluid tray for use in the penicillin allergy test kit of the present invention, comprising a multi-site skin-test applicator having four applicators with scratching barbs pointing downward, cooperatively engaged with a fluid tray, the multi-site skin-test applicator having four scratching barbs that simultaneously scratch the skin of the patient as trace amounts of allergy test fluids are inserted into the skin of the patient, the multi-site skin-test applicator being disposed on the fluid tray; and DETAIL "B" depicting an exploded side view of the scratching barb positioned in a reservoir of the fluid tray during loading of allergy test fluids, the reservoir being partially filled with an allergy test fluid.

FIG. 11A is a front view of the multi-site skin-test applicator in an expanded position with the scratching barbs, the pair of opposing scratching barbs now being loaded, and each scratching barb including a trace of their respective allergy test fluid prepared for deposition of allergy test fluids.

FIG. 11B is a front view of the multi-site skin-test applicator of FIG. 13A, the multi-site skin-test applicator now being in a compressed position. The scratching barbs are resting upon the skin of a patient with the pair of opposing scratching barbs pointed downward.

FIG. 11C is a front view of the multi-site skin-test applicator of FIG. 13B, the multi-site skin-test applicator now being in an expanded position, the scratching barbs now have generated a pair of scratches at a pair of test sites as the pair of opposing scratching barbs move away from each other.

DETAILED DESCRIPTION OF THE INVENTION

Figure 1:
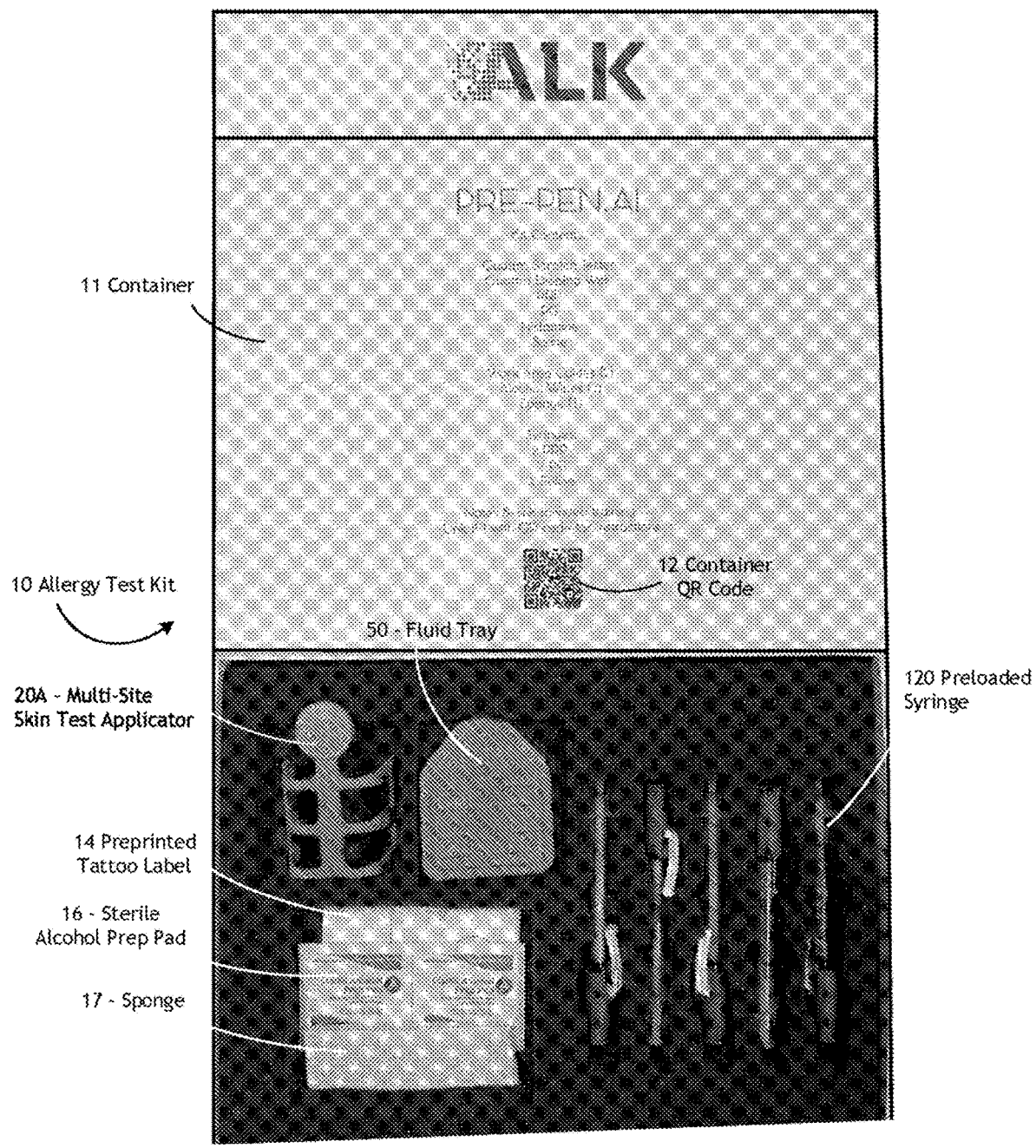
FIG. 1 is a preferred embodiment of an assembly view the penicillin allergy test kit of the present invention, including a container, a multi-site skin test applicator and fluid tray, five preloaded syringes, and a tattoo-type label that is transferable onto the skin of the patient. One syringe is preloaded with saline, two syringes are preloaded with Pre-Pen, and two syringes are preloaded with Pen-G.

Referring now to the drawings, FIG. 1 is a preferred embodiment of an assembly view the penicillin allergy test kit of the present invention [10].

The test kit of the present invention [10] comprises a container [11], a multi-site skin test applicator [20A] and fluid tray [50], five preloaded syringes [60], and a tattoo-type label [14] that is transferable onto the skin of the patient.

Each container [11] and each tattoo-type label [14] includes a machine-readable code. The machine-readable code of choice for the allergy test kit of the present invention is a QR Code. Other machine-readable codes include but are not limited to DataMatrix, Aztec, Beetagg, mCode, Shotcode, Quickmark, and TrillCode.

Each of the five preloaded syringes [60] is identified as to content. Also, each of the five preloaded syringes [60] being placed in a specific location in the test kit [10]. One syringe is preloaded with saline, two syringes are preloaded with Pre-Pen, and two syringes are preloaded with Pen-G.

The allergy test kit of the present invention [10] also includes a pair of preprinted tattoo labels [14], and the multi-site skin test applicator [20A] and fluid tray [50] of FIG. 1.

The allergy test kit of the present invention [10] preferably also includes a sponge [17] and two sterile alcohol prep pad [16].

The penicillin allergy test kit [10] is stored conveniently in a leak-proof sealed container [11]. The penicillin allergy test kit [10] includes five preloaded syringes [60], each syringe being identified as to content, and each being placed in a specific location in the tester kit [10]. One syringe is preloaded with saline, two syringes are preloaded with Pre-Pen, and two syringes are preloaded with Pen-G. The penicillin allergy test kit [10] also includes a plurality of preprinted tattoo labels [14], a pair of sterile alcohol prep pads [16], and the multi-site skin test applicator [20A] and fluid tray [50] of FIG. 1 for the penicillin allergy test kit of the present invention.

Figure 2:
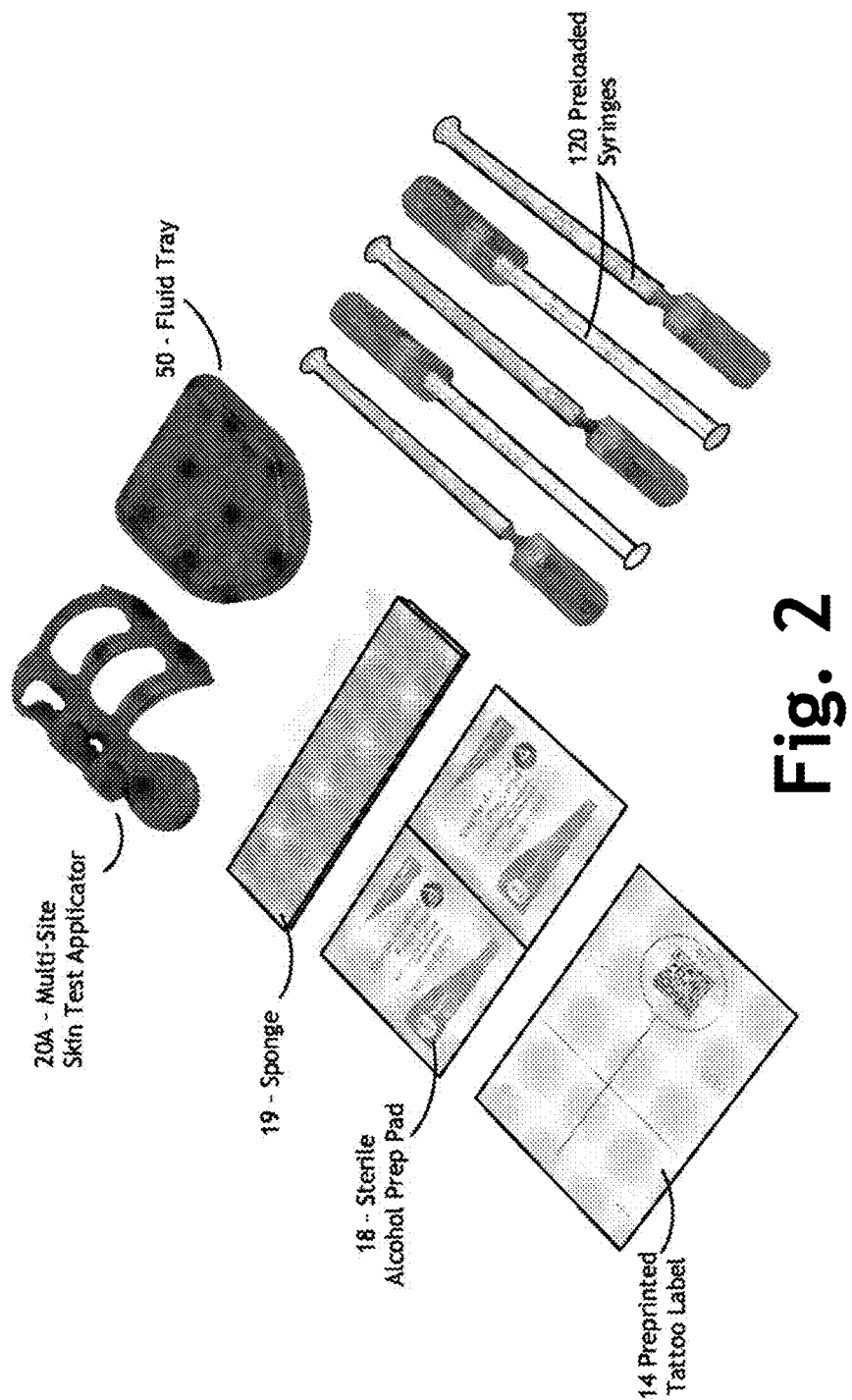
FIG. 2 is a preferred embodiment of an assembly view depicting the contents of the penicillin allergy test kit of FIG. 1, the test kit being stored conveniently in a leak-proof sealed container, the kit including five preloaded syringes, each syringe being identified as to content and each being placed in a specific location in the tester kit—one syringe being preloaded with saline, two syringes being preloaded with Pre-Pen, and two syringes being preloaded with Pen-G, preprinted tattoo labels, a pair of sterile alcohol prep pads, and the multi-site skin-test applicator and fluid tray.

FIG. 2 is a preferred embodiment of an assembly view depicting the contents of the penicillin allergy test kit [10] of FIG. 1. The penicillin allergy test kit [10] is stored conveniently in a leak-proof sealed container [11].

The allergy test kit [10] preferably includes five preloaded syringes [60], each syringe being identified as to content, and each being placed in a specific location in the tester kit container [10]. One syringe is preloaded with saline, two syringes are preloaded with Pre-Pen, and two syringes are preloaded with Pen-G. The allergy test kit [10] also includes a plurality of preprinted tattoo labels [14], a pair of sterile alcohol prep pads [16], and the multi-site skin-test applicator [20A] and a fluid tray [50] of FIG. 1 for the allergy test kit of the present invention [10].

Figure 3:
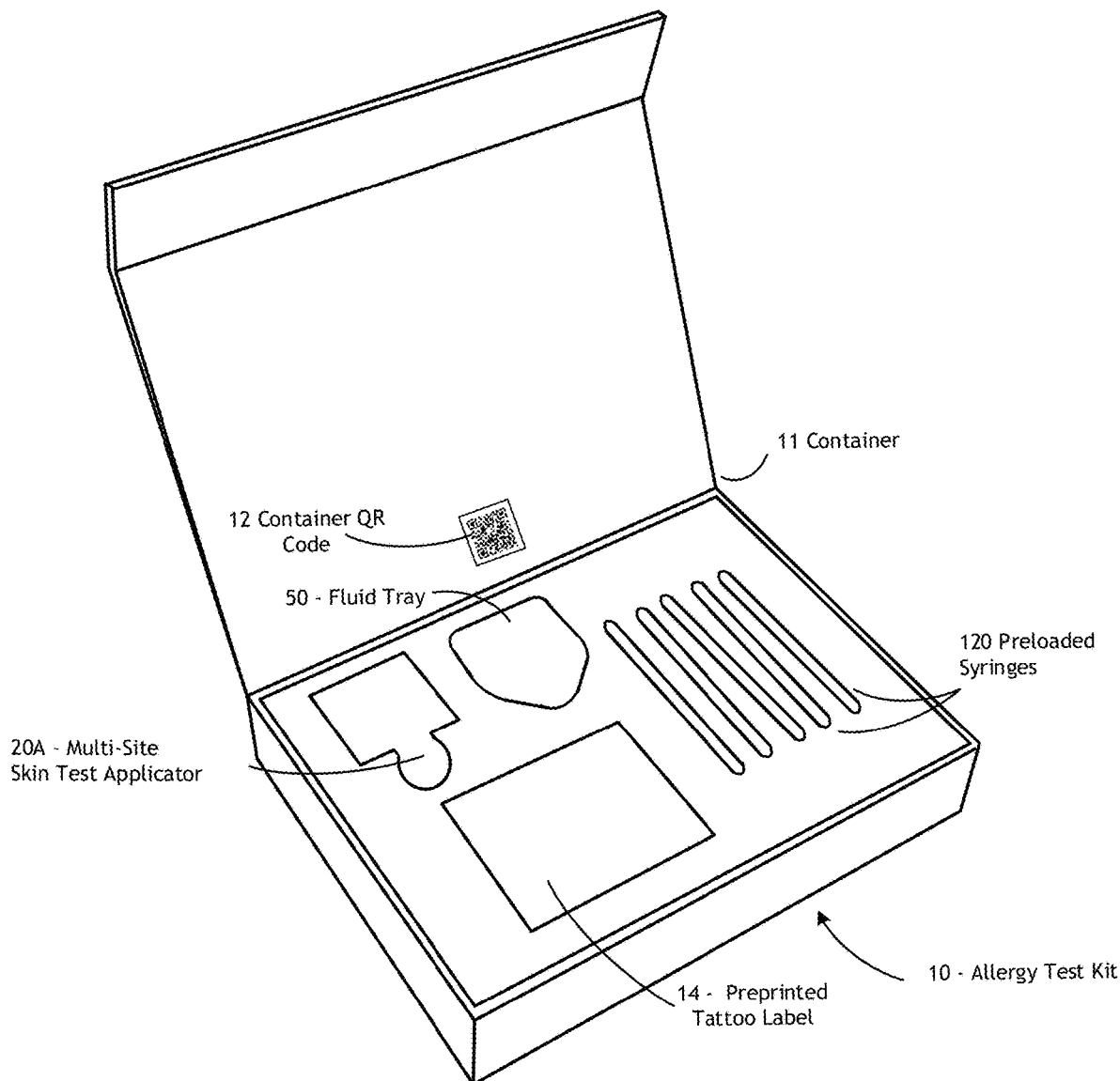
FIG. 3 depicts a first preferred embodiment of the container of the penicillin allergy test kit of FIG. 1, the container lid being open and the container being empty.

FIG. 3 depicts a first preferred embodiment of the container of the penicillin allergy test kit of FIG. 1, the container lid being open and the container being empty.

Figure 4A:
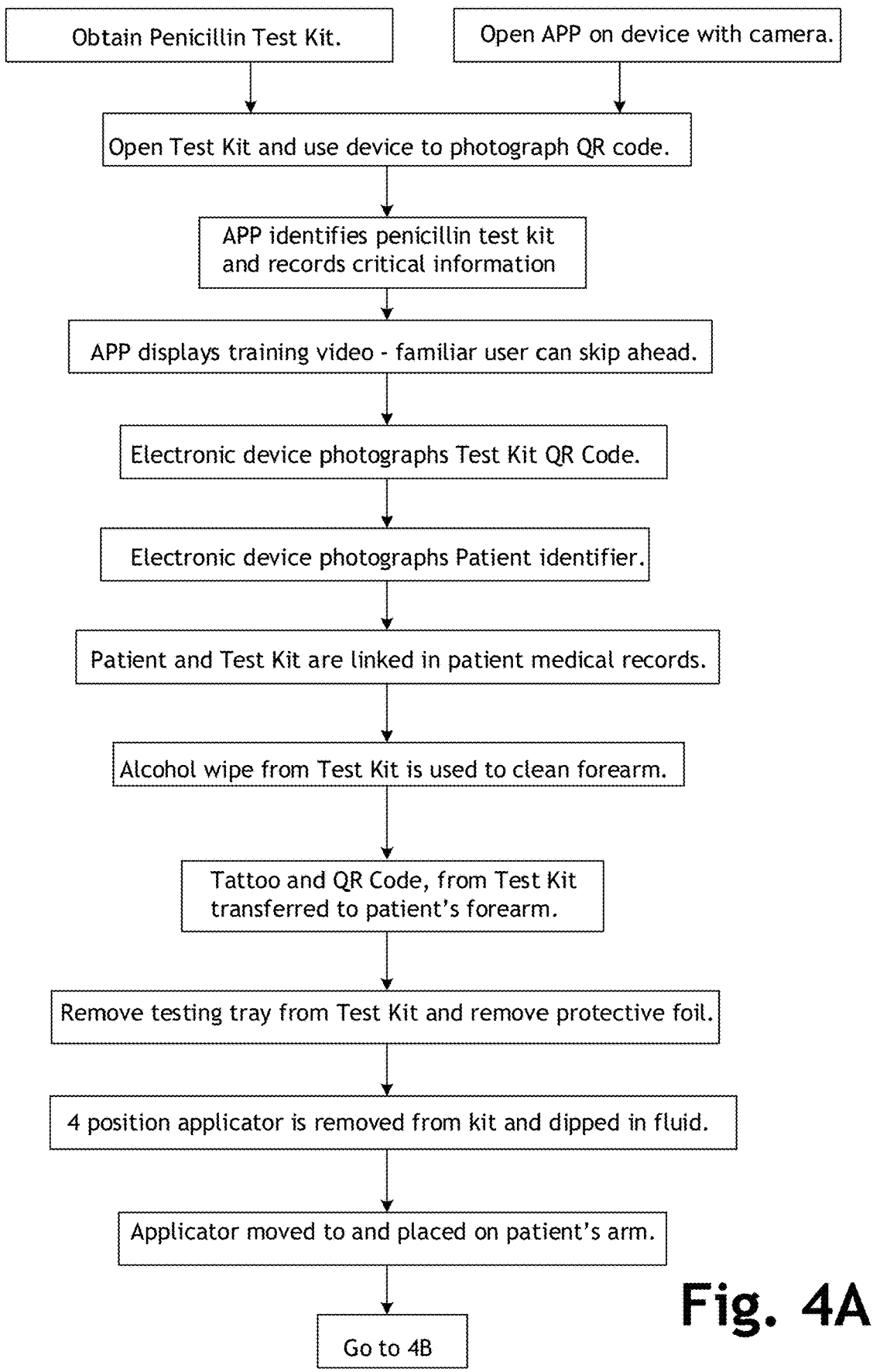
FIGS. 4A, 4B, and 4C depict a simplified flowchart showing the way the preferred embodiment for using the allergy test kit of the present invention to determine penicillin allergies of a patient.
Figure 4B:
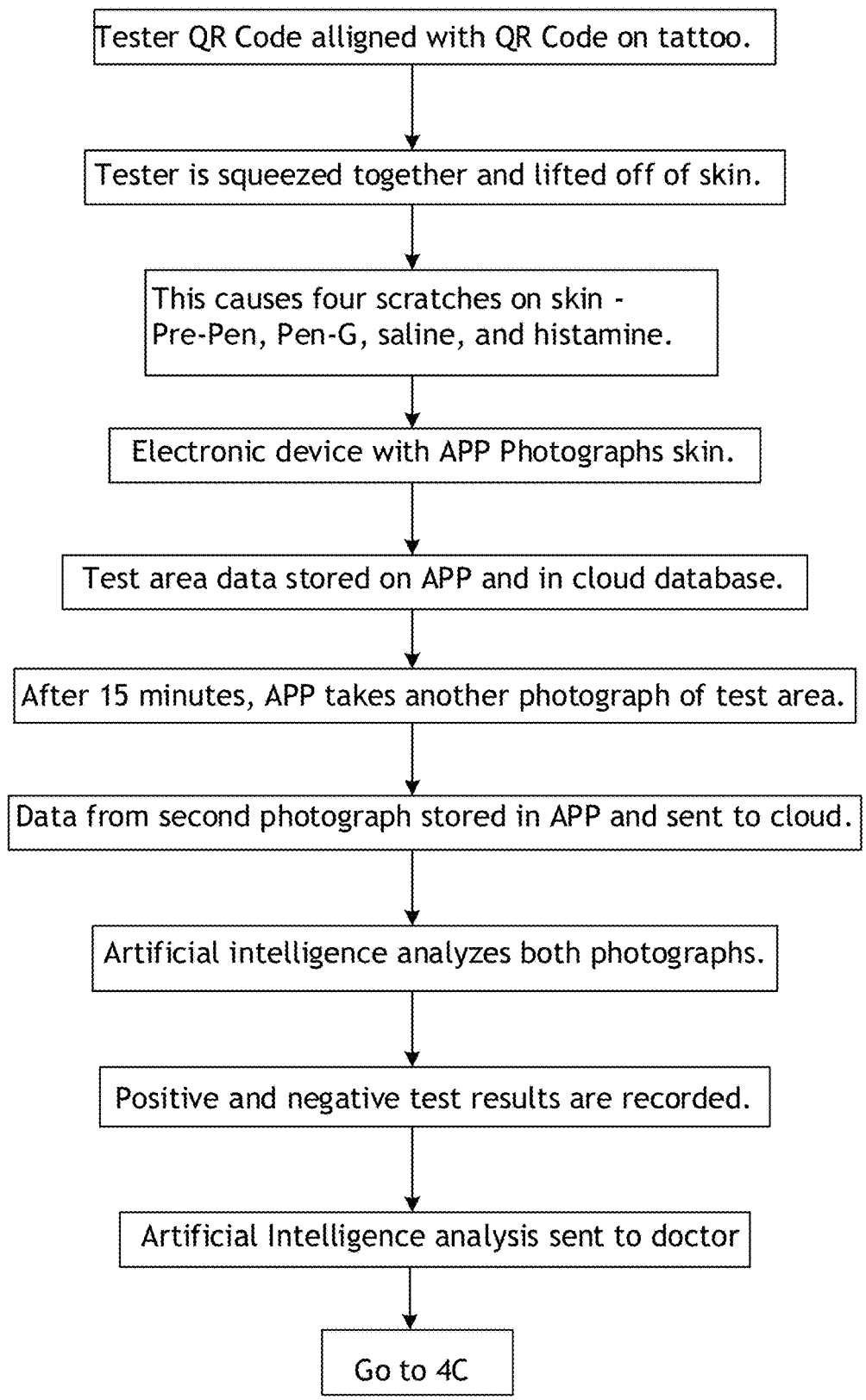
Figure 4C:
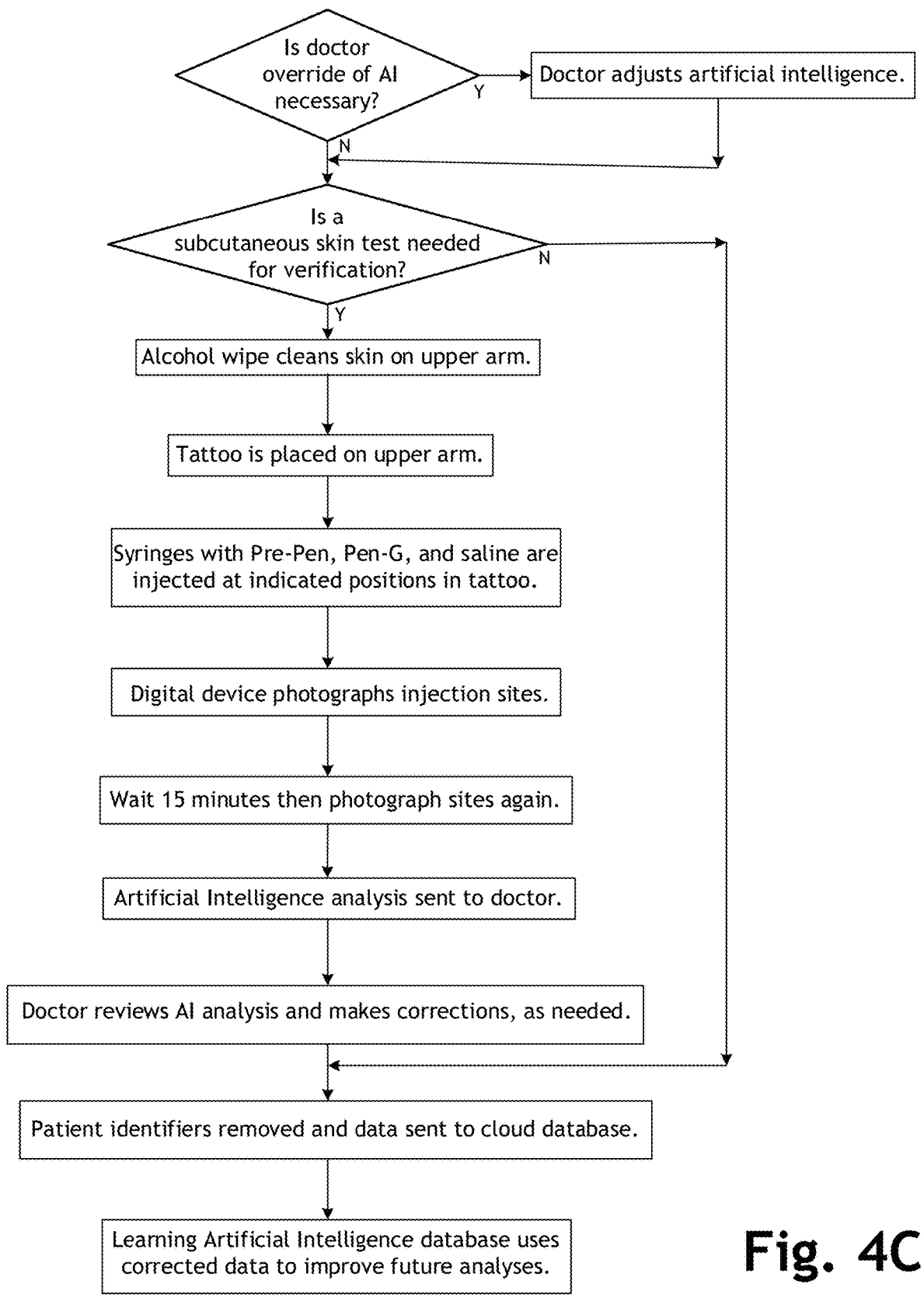

FIGS. 4A, 4B, and 4C depict a simplified and detailed flowchart showing the way the preferred embodiment for using the allergy test kit of the present invention to determine penicillin allergies of a patient. The allergy test kit of the present invention enables the doctor to review the artificial intelligence being provided by the system for this patient (see FIG. 4C). The doctor reviews the artificial intelligence analysis and decides either to accept the analysis or modify it. If a modification is made, the doctor can indicate why the modification was necessary. The doctor may also decide to verify negative results with a subcutaneous skin test, whereby one or more of the preloaded syringes are inserted into the skin of the patient (see FIG. 4C).

Figure 5:
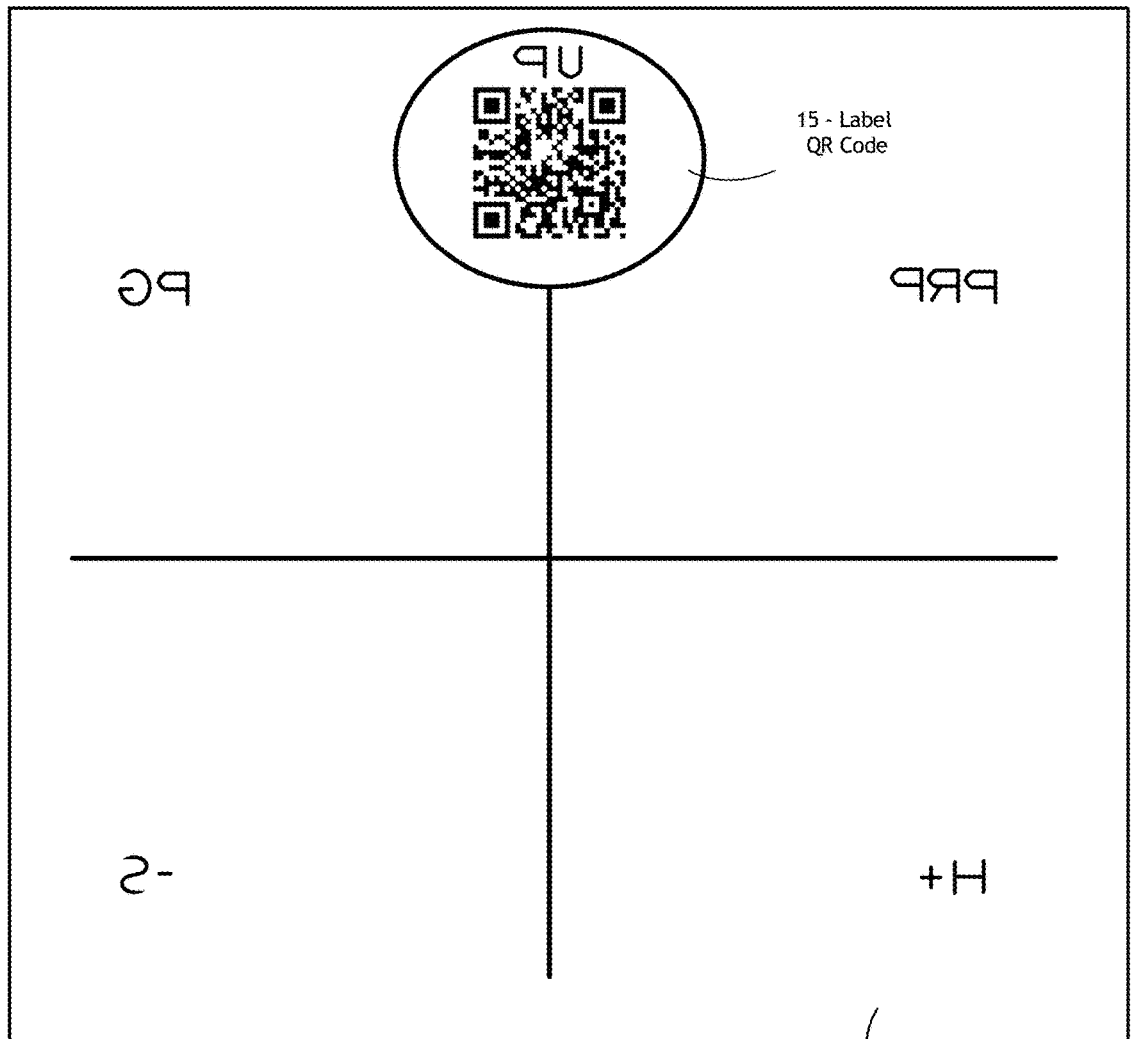
FIG. 5 is a preferred embodiment of a preprinted tattoo label for use with the penicillin allergy test kit of the present invention, the preprinted tattoo label is for placement and transfer on a forearm or an upper arm of a patient and includes a QR Code, each preprinted tattoo label identifies a scratch test, and identifies the saline, the histamine, the Pre-Pen, and the Pen-G.

FIG. 5 is a preferred embodiment of a preprinted tattoo label [14] for use with the allergy test kit of the present invention [10]. The preprinted tattoo label [14] is for placement for transfer on the skin of the patient, preferably a forearm or an upper arm. Each preprinted tattoo label [14] is temporary and includes a QR Code [15]. Each tattoo label [14] is divided into quadrants for the allergy test fluids, and identifying the quadrant for the saline, the histamine, the Pre-Pen, and the Pen-G.

Figure 6:
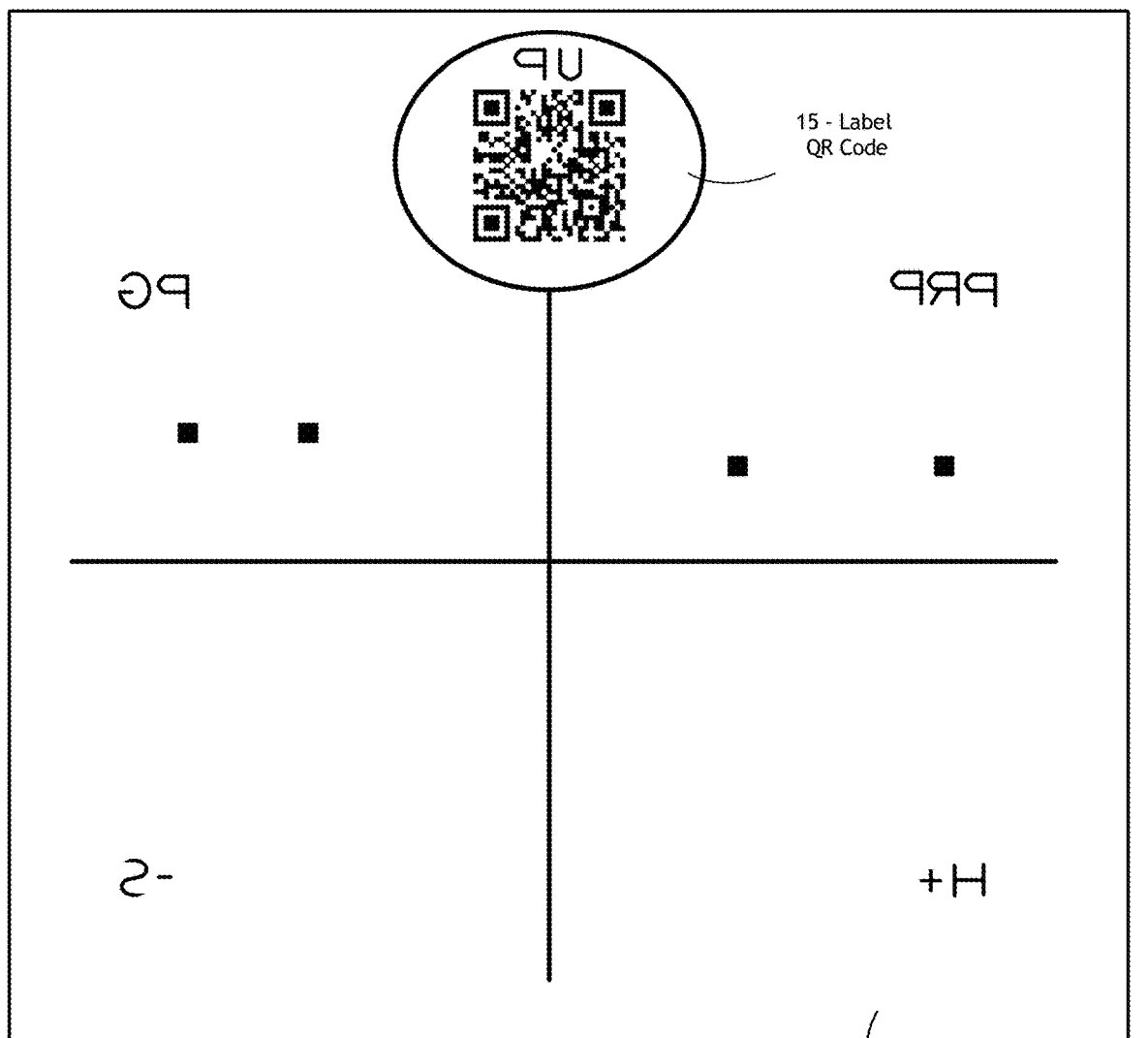
FIG. 6 is a preferred embodiment of the preprinted tattoo label of FIG. 5 for use with the five preloaded syringes of the penicillin allergy test kit of the present invention.
Figure 7:
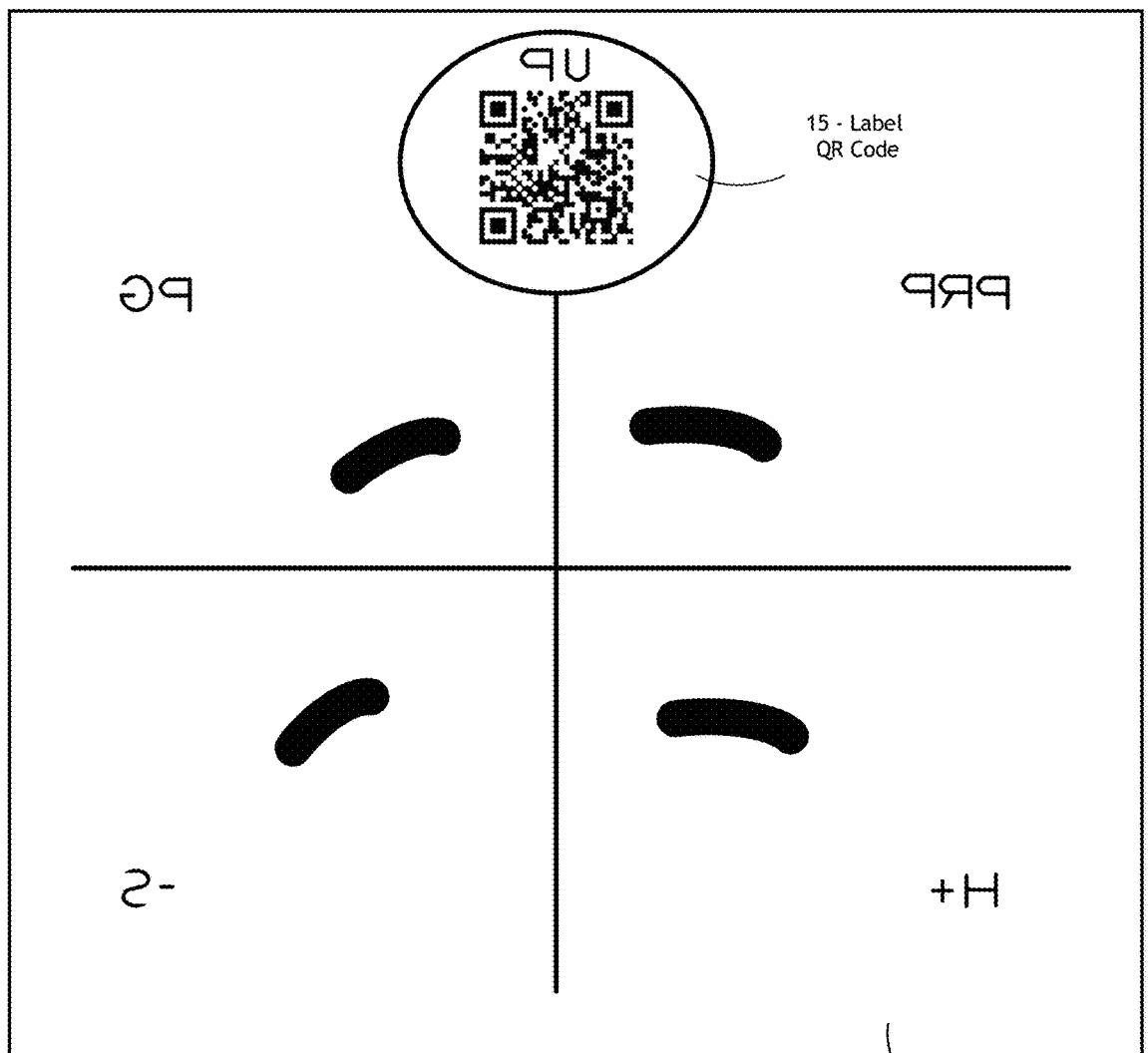
FIG. 7 is a preferred embodiment of the preprinted tattoo label of FIG. 5 for use with the multi-site skin-test applicator of the penicillin allergy test kit of the present invention, the preprinted tattoo label depicts the smears of the test results from the multi-site skin-test applicator for the four skin tests are of the saline, the histamine, the Pre-Pen, and the Pen-G.

FIGS. 6 and 7 are preferred embodiments of the preprinted tattoo label [14] of FIG. 5 for use with the multi-site skin-test applicator of the penicillin allergy test kit of the present invention of the present invention. FIG. 6 depicts the preprinted tattoo label with the location of the test injection sites from the five preloaded syringes [60] being disposed in the appropriate quadrants of the tattoo. In one preferred embodiment, the container QR Code [12] matches the label QR Code [15]. FIG. 7 depicts the preprinted tattoo label [14] with the smears of the test results from the multi-site skin-test applicator [20A] for the four skin tests disposed in the appropriate quadrants of the tattoo.

FIG. 8 depicts an assembly view of a first preferred embodiment of a multi-site skin-test applicator and fluid tray for use in the allergy test kit of the present invention, comprising a first preferred embodiment of the multi-site skin-test applicator having four applicators cooperatively engaged with a fluid tray, the multi-site skin-test applicator having four scratching barbs that simultaneously scratch the skin of the patient as trace amounts of allergy test fluids are inserted into the skin of the patient, the multi-site skin-test applicator being disposed on the fluid tray. DETAIL "A" depicts an exploded side view of the scratching barb positioned in a reservoir of the fluid tray during the loading of allergy test fluids, the reservoir being partially filled with an allergy test fluid.

The multi-site skin-test applicator [20A] includes a centrally disposed spine [21] and pair of side handles [30 and 31] along a pair of opposing finger grips [35 and 36]. A pair of opposed handle arms [32] extend downward on each side of the spine [21] and a pair of handle legs [35] extend downward from each side handle [30]. Disposed at an end of each handle leg [34] is an upward-projecting scratching barb [40A and 40B]. DETAIL "A" depicts a scratching barb [40B] disposed in a reservoir [52]. There are four reservoirs [52], two rows of two each on the fluid tray [50].

Two scratching barbs pointed upward [40A and 40B] oppose each other and cooperatively engage with each other to simultaneously generate two small scratches [91] on the skin of the patient while depositing trace amounts of allergy test fluids at their respective test sites.

FIGS. 9A, 9B, and 9C depict the first embodiment of the multi-site skin-test applicator [20A] of the present invention during allergy barb deposition. When subsequently repositioned upon the skin of the patient [90], the pair of opposing scratching barbs [40A and 40B] contact both sides of the raised portion of the skin [94] of the patient.

FIG. 9A is a front view of the multi-site skin-test applicator [20A] in an expanded position, with the pair of opposing scratching barbs [40A and 40B] resting upon the skin of a patient [90]. The multi-site skin-test applicator [20A] is in an expanded position. The scratching barbs [40A and 40B] each include a trace of their respective allergy test fluids and are prepared for allergy test fluid barb deposition.

FIG. 9B is a front view of the multi-site skin-test applicator [20A]. The multi-site skin test applicator is now being in a compressed position by use of the pair of finger grips [35 and 36]. The pair of opposing scratching barbs [40A and 40B] are resting upon the skin of the patient [90] with the each of pair of opposing scratching barbs [40A and 40B] disposed about a portion of the skin of a patient [90] that has been lifted upwards [94] between the pair of opposed scratching barbs [40A and 40B]. The multi-site skin-test applicator [20A] is in the allergy test fluid deposition position.

FIG. 9C is a front view of the multi-site skin-test applicator [20A] of FIG. 8. The multi-site skin-test applicator [20A] is still being compressed. The pair of opposing scratching barbs [40A and 40B] now have been raised upward from the skin of the patient [90] with small scratches [91] now appearing on each side of the portion of the skin of the patient that was lifted upwards [94].

With the pair of opposing scratching barbs [40A and 40B] now positioned on the skin of the patient [90], the multi-site skin-test applicator [20A] is moved from the relaxed state to the compressed state and pulled upwards away from the raised skin. In so doing, the pair of opposing scratching barbs [40A and 40B] will break the skin of the patient [90] and generate a plurality of small scratches [91]. A trace amount of each allergy test fluid [57] has been retained on each scratching barb [40A and 40B] and is inserted into each scratch [91] on the skin of the patient [90].

The method of administering the plurality of allergy test fluids using the multi-site skin test system requires allergy test fluid barb loading (the position [25] being depicted in DETAIL "A" of FIG. 8) and allergy test fluid barb deposition (the position [92] being shown in FIG. 9C).

FIG. 10 depicts an assembly view of a second preferred embodiment of a multi-site skin-test applicator [20B] and fluid tray [50] for use in the penicillin allergy test kit of the present invention [10]. The multi-site skin-test applicator [20B] has four scratching barbs [49A and 40B] pointing downward, cooperatively engaged with the fluid tray [50], the multi-site skin-test applicator [20B] having four scratching barbs [40B] that simultaneously scratch the skin of the patient as trace amounts of allergy test fluids are inserted into the skin of the patient. The multi-site skin-test applicator [20B] is disposed on the fluid tray [50]. DETAIL "B" depicting an exploded side view of the scratching barb positioned in a reservoir of the fluid tray [50] during allergy test fluid loading, the reservoir [54] being partially filled with an allergy test fluid.

The multi-site skin-test applicator [20B] includes a centrally disposed spine [21] and pair of side handles [30 and 31] along a pair of opposing finger grips [35 and 36]. A pair of opposed handle arms [32] extend downward on each side of the spine [21] and a pair of handle legs [35] extend downward from each side handle [30]. Disposed at an end of each handle leg [34] is a downward-projecting scratching barb [42A and 42B]. DETAIL "B" depicts a scratching barb [42B] disposed in a reservoir [54]. There are four reservoirs [54], two rows of two each on the fluid tray [50].

FIG. 11A is a front view of the multi-site skin-test applicator in an expanded position with the scratching barbs, the two scratching barbs now being loaded and each scratching barb includes a trace of their respective allergy test fluid prepared for allergy test fluid deposition.

Two scratching barbs pointed downward [42A and 42B] oppose each other and cooperatively engage with each other to simultaneously generate two scratches on the skin of the patient while depositing trace amounts of allergy test fluids at their respective test sites.

FIGS. 11A, 11B, and 11C depict an alternate embodiment of the method for administering multiple allergy test fluids of the present invention, each pair of opposing scratching barbs [42A and 42B] of the multi-site skin-test applicator [20B] pointed downward toward the fluid tray [50] when disposed in the fluid tray [50]. The fluid tray [50] contains multiple allergy test fluids disposed in each reservoir [54] respectively. Allergy test fluids [57] are selected and placed in reservoirs [54] in the fluid tray [50], and care is taken not to use an excess amount of the allergy test fluids. After allergy test fluid barb loading is completed, the medical technician lifts the multi-site skin-test applicator [20B] out of the fluid tray [50], the multi-site skin test applicator [10] being in the relaxed state. Using the pair of opposing finger grips [30 and 31], the medical technician applies pressure moving the multi-site skin-test applicator [20B] to a compressed state before placing the multi-site skin-test applicator [20B] upon the skin of the patient [90] in the allergy test fluid deposition position. The medical technician then pushes lightly upon the multi-site skin-test applicator [20B] and slowly releases the finger grips [30 and 31]. This generates a scratch [91] at each test site essentially simultaneously on the skin of the patient [90]. Trace amounts of each respective allergy test fluid [57] then seep into each respective scratch [91]. The use of the finger grips [30 and 31] to move the multi-site skin-test applicator [20B] from the relaxed state to the compressed state and then back again to the relaxed state enables one-handed operation by the medical technician. Then, the multi-site skin-test applicator [20B] is pulled up and away from the skin of the patient [90].

FIG. 11A is a front view of the multi-site skin-test applicator [20B] in an expanded position, with the pair of opposing scratching barbs [42A and 42B]. The pair of opposing scratching barbs [42A and 42B] are loaded, each including a trace amount of allergy test fluid and are prepared for allergy test fluid deposition. FIG. 11B is a front view of the multi-site skin-test applicator [20B], which is now in a compressed position. The pair of opposing scratching barbs [42A and 42B] are resting upon the skin of a patient [90] with the pair of opposing scratching barbs [42A and 42B] pointed downward. FIG. 11C is a front view of the multi-site skin-test applicator [20B], which is now in an expanded position. The pair of opposing scratching barbs [42A and 42B] now have generated a pair of scratches [91] on the skin of the patient [90] at a pair of test sites as the pair of opposing scratching barbs [42A and 42B] move away from each other.

FIG. 11B is a front view of the multi-site skin-test applicator of FIG. 13A, the multi-site skin-test applicator now being in a compressed position. The scratching barbs are resting upon the skin of a patient with the each of two scratching barbs pointed downward.

FIG. 11C is a front view of the multi-site skin-test applicator of FIG. 13B, the multi-site skin-test applicator now being in an expanded position, the scratching barbs now have generated a pair of scratches at a pair of test sites as the scratching barbs move away from each other.

Figure 12A:
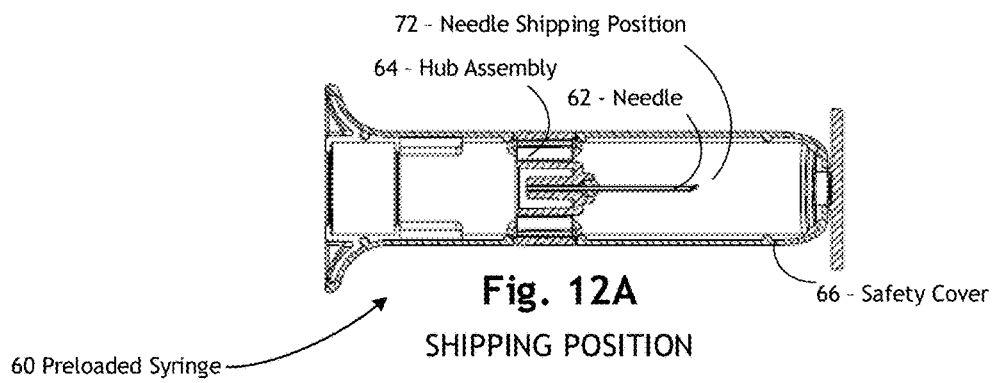
FIG. 12A depicts a side elevational view of a first preferred embodiment of a safety syringe for use with the multi-site skin-test applicator of FIG. 1, with a needle hub assembly in a needle shipping position. The unused needle is locked in and protected by a safety cover.
Figure 12B:
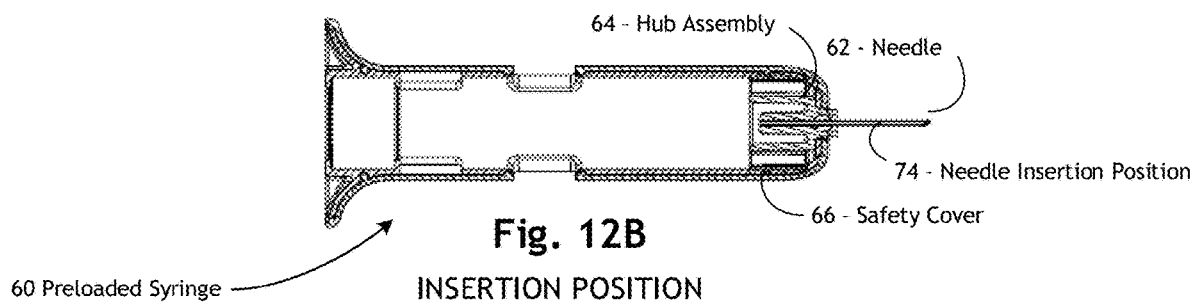
FIG. 12B depicts a side elevational view of the safety syringe for use with the multi-site skin-test applicator of FIG. 1, with the needle hub assembly being disposed in a second and forward secured needle insertion position for insertion of the needle into the skin of the patient.
Figure 12C:
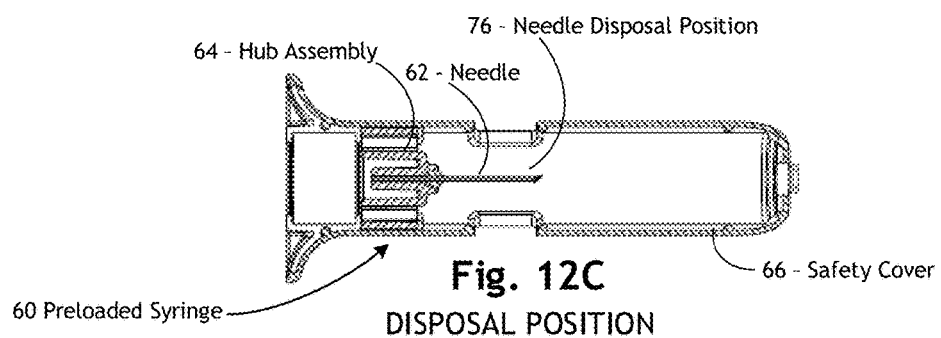
FIG. 12C depicts a side elevational view of the safety syringe for use with the multi-site skin-test applicator of FIG. 1, with a needle hub assembly in a third secured position. The safety syringe has been used and is awaiting disposal. The used needle is locked in and protected by the safety cover.

The penicillin allergy test kit of the present invention [10] preferably includes five preloaded safety syringes [60], to enable additional subcutaneous skin testing if the doctor deems such testing necessary. While there are several different suitable syringes available, the syringe of choice is disclosed in U.S. Pat. Nos. 10,973,990 and 10,765,814 (Prince). FIG. 12A depicts a side elevational view of a first preferred embodiment of a safety syringe [60] for use with the multi-site skin-test applicator [20A] of FIGS. 8 and 10, with a needle hub assembly in a needle shipping position [72]. The unused needle [62] is locked in and protected by a safety cover [66]. FIG. 12B depicts a side elevational view of the safety syringe [60] for use with the multi-site skin-test applicator [20A] of FIGS. 8 and 10, with the needle hub assembly [64] being disposed in a second and forward secured needle insertion position [74] for insertion of the needle [62] into the skin of the patient. FIG. 12C depicts a side elevational view of the safety syringe [60] for use with the multi-site skin-test applicator [20A] of FIGS. 8 and 10, with a needle hub assembly in a third secured position. The safety syringe [60] has been used and is awaiting disposal. The used needle [62] is locked in and protected by the safety cover [66].

The penicillin allergy test kit of the present invention [10], including five preloaded syringes [60], each syringe being identified as to content, and each being placed in a specific location in the tester kit [10]. One syringe is preloaded with saline, two syringes are preloaded with Pre-Pen, and two syringes are preloaded with Pen-G.

U.S. Pat. No. 6,554,777 (Hein, Jr.) discloses a multi-site skin-test system. The system includes a reservoir tray and strips of interconnected reservoir caps inserted into upper portions of the reservoirs. The caps each include a generally conically shaped hole. Connection members connect the caps of a strip to one another. The strips of caps are pressed into tightly fitting upper portions of reservoirs having upwardly facing ledge surfaces for supporting downwardly facing bottom surfaces of the caps. The outer side surfaces of the caps and the inner surfaces of the upper portions of the reservoirs are substantially the same size to provide a tight fit. A tray lid includes a downwardly extending ridge that cooperates with the tray to prevent the lid from being placed onto the tray backwards.

U.S. Pat. No. 5,551,441 (Pitesky) discloses a multi-site skin-test system. The injection pick holder to releasably holds and applies to a patient a plurality of allergy test fluids. The puncture-type device includes a block member having upper and lower ends and side walls, the lower end having formed thereon a pair of parallel longitudinal downwardly opening slits and a plurality of sockets formed on each of the slits in spaced relation. A pair of upwardly and outwardly angling hand grasp ears project from the diametrical opposite longitudinal sides of the upper end. A multi-elastic band encompasses the peripheral side walls and is continually in tension when it is in place.

However, the preferred multi-site skin test system is a variation of the system disclosed in U.S. patent application Ser. No. 17/468,132 (Prince) having four scratching barbs cooperatively engaged with four reservoirs in the fluid tray. The multiple allergen testing system includes an applicator and a fluid tray. The fluid tray is cooperatively engageable with the applicator. The applicator has an allergen loading position and an allergen deposition position. In the allergen loading position, a different allergen is loaded onto each respective scratching barb from each respective reservoir of the loading tray. Each scratching barb is designed to retain a trace of allergen fluid. A pair of finger grips are positioned on opposing sides of the applicator frame. The applicator fits into one hand of a medical technician administering the allergen skin testing. The applicator is removed from the fluid tray and repositioned onto the skin of the patient. The applicator is made of compressible material. In the allergen deposition position, the applicator is compressed, and each allergen is deposited into each respective scratch generated by each respective scratching barb on the skin for further analysis.

There are two methods of intracutaneous application of allergy test fluids, (1) the puncture method and (2) the abrasion or scratching method. U.S. Pat. No. 6,554,777 (Hein, Jr.) and U.S. Pat. No. 5,551,441 (Pitesky) use the puncture method and U.S. patent application Ser. No. 17/468,132 (Prince) uses the abrasion or scratching method. While the allergy test kit [10] of the present invention is compatible with all three systems, the preferred system deploys the kit shown in U.S. patent application Ser. No. 17/468,132 (Prince). Accordingly, for purposes of illustration and simplicity, this test kit [10] with this multi-site skin test system [18A and 18B] is depicted in the drawings accompanying this Application. However, it is to be understood that these other devices can also be used and are not waived hereby.

The multi-site skin-test system [18A] is built around the multi-site skin-test applicator [20A] that enables the accurate and repeatable placement of the allergy testing fluid from the fluid tray [50]. Then, these allergy test fluids are transferred to the scratching barbs [40A and 40B] of the multi-site skin-test applicator [20A] from the fluid tray [50].

Once the scratching barbs [42A and 42B] of the multi-site skin-test system [18A] are on the skin of the patient, the multi-site skin-test applicator [20A] is moved in such a way as to lift the skin in front of the scratching barbs [40A and 40B].

When the medical professional decides that a patient requires a test for an allergic reaction to penicillin, he gets a penicillin allergy test kit of the present invention and opens the APP on a smart phone, a tablet or other electronic device that has the APP installed. The test box is opened, and the APP is started. The device's camera is pointed at the QR Code on the inside of the penicillin test kit container and a photograph of the QR Code is taken. The APP interprets the code as being a penicillin allergy test kit and records the test kit information, such as kit code, date code, manufacturer, date, etc. The APP then leads the medical professional to a short training video which walks them through the proper use of the penicillin allergy test kit of the present invention. The patient will have a QR Code, a bar code or any other digital identifier associated with their electronic medical records, that will be scanned by the APP. The APP now associates the particular penicillin allergy test kit of the present invention with the patient.

An alcohol wipe is removed from the kit and is used to cleanse the forearm of the patient. The first tattoo is placed on the forearm of the patient. This tattoo transfers the identical QR Code from the container onto the forearm of the patient. The tattoo also identifies four testing quadrants: one for Pre-Pen (PRP), one for Pen-G (PG), one for saline (−) and one for histamine (+). The saline and histamine are the controls in the test. The saline will always give a negative reaction and the histamine will always give a positive reaction. The positive reaction of the histamine will be a wheal that grows 3 to 5 millimeters in diameter from the initial size of the bleb (the raised skin blister caused by the fluid being injected under the skin). The skin will also show a red color or flair, which is an indication of a positive reaction to the histamine. The saline being negative and the histamine being positive indicates that the patient has not taken any antihistamine (such as Benadryl®) in recent days and that the penicillin test will not be affected by an antihistamine in the system of the patient.

The medical professional then removes the allergen testing tray from the kit and removes the protective covering from the top. The tattoo is then transferred to the forearm of the patient. The medical professional then takes the multi-site skin-test applicator from the penicillin allergy test kit of the present invention, dips the ends of the multi-site skin-test applicator into the four reservoirs of the fluid tray, being certain that the UP mark on the multi-site skin-test applicator is aligned with the UP mark on the fluid tray.

The multi-site skin-test applicator with a trace of the testing fluid on each scratching barb is placed on the skin, in the correct quadrant. This is ensured by placing the circular up indicator of the multi-site skin-test applicator above the circular up mark on the tattoo. The scratching barbs are placed on the skin, light pressure is applied, and the arms of the tester are pulled towards each other and then lifted, scratching the skin of the patient, and applying a small amount of allergy test fluid into the scratched skin area. Any excess fluid can be blotted from the skin, taking care not to cross contaminate the testing areas of the skin of the patient. The electronic device, running the testing APP will take a photograph of the test area immediately after the scratch test.

The APP records the skin color and the size of each wheal caused by the scratch tester. A 15-minute timer is started. After 15 minutes, the APP takes another photograph of the scratch test site. Artificial intelligence which has been built into the APP, analyzes each scratch test site. The saline must be negative, the histamine must be positive, and the areas scratched by the Pre-Pen and Pen-G will indicate a positive reaction or a negative reaction. A positive reaction is indicated by the wheal growing by 3 to 5 mm and having a red color or flair. The APP records the results, associates the results with the patient and suggests a positive or a negative for each of the test sites and grades them from 0 to 4. The doctor reads the suggested artificial intelligence results and decides on the next course of action. The doctor may decide to confirm any negative test results by performing a subcutaneous retest. This test is done by injecting a small amount of Pre-Pen at two sites on the upper arm, injecting Pen-G at two sites on the upper arm and saline injected at one place on the upper arm. The medical professional removes the alcohol wipe [16] from the test kit and cleanses the upper arm of the patient, and then applies the tattoo [14] to the upper arm.

With the tattoo [14] in place, the first Pre-Pen, preloaded syringe [60] is removed from the container [11] of the allergy test kit of the present invention [10]. The Pre-Pen allergy test fluid is injected under the skin of the patient in the tattoo quadrant marked "Pre-Pen". The used syringe is closed into its locked, disposal, position and placed back into the container. The second Pre-Pen syringe is removed from the container and injected under the skin in the quadrant marked "Pre-Pen". The syringe is then returned to the container [11]. The first Pen-G syringe is removed from the container and the allergy test fluid is injected under the skin of the patient in the quadrant marked "Pen-G". The syringe is then returned to the container [11]. Next, the second Pen-G syringe is removed from the container and the allergy test fluid is injected under the skin of the patient in the quadrant "Pen-G". The syringe is then returned to the container [11]. And finally, the saline syringe is removed from the test kit and the saline is injected under the skin of the patient in the quadrant marked "S-". The digital device then photographs the upper arm tattoo area, the QR Code, of the allergy test kit of the present invention [10] being recorded and is digitally connected to the patient.

After 15 minutes, the digital device is used to take another photograph of the upper arm tattoo area and the site of the 5 injections. The artificial intelligence built into the APP analyzes the test site, measures the wheal change size and the red flair and grades the reaction from 0 to 4. The QR Code for this test is the kit QR Code and is tied to the patient's electronic health records. The doctor reviews the artificial intelligence results and either approves the results or modifies them. Then the medical professional having the test results, treats the patient as recommended. The test results now follow the patient. With all the contents of the penicillin allergy test kit of the present invention now being returned to the container, the foam around each component will absorb any fluids remaining in the scratch test wells, on the four-position applicator unit [20] and in the syringes. The container can be closed. When the container is closed, it will lock and seal itself, transforming the container into its own sharps container. The container and its contents are then discarded as one would discard a full sharps container for proper disinfecting and disposal.

The next step is to strip any patient specific data from each test (scratch and subcutaneous), keep artificial intelligence's initial grades, photographs and data, also keep the changes made by the doctor and transmit this data to a worldwide data base. Artificial intelligence that operates and controls the database, reviews initial gradings for artificial intelligence, the photographs and data as well as the changes made by the doctor to improve future diagnoses. This is a form of machine learning, but this learning is taught by the corrections the doctor makes. As more test data is added to the database, the artificial intelligence gets smarter and will continually improve its initial diagnoses.

A positive test result indicates a high likelihood of penicillin allergy. A negative test result usually means the patient is not at high risk of an allergy to penicillin. But a negative result is more difficult to interpret since some drug reactions cannot be detected by skin tests.

Artificial intelligence is used in the penicillin allergy test kit of the present invention. Other systems that deploy similar-type artificial intelligence systems to assist medical professionals in decision-making and machine learning include:

U.S. Pat. No. 11,037,682 (Kelly et al.) depicts a dynamic selection and sequencing of healthcare assessments for patients. Mechanisms are provided for administering health care assessments to a patient. The mechanisms analyze patient information stored in a patient registry and determine a plurality of health care assessments to be administered to the patient based on the patient information and one or more pre-defined health care assessment guidelines specifying conditions for which health care assessments are to be administered to patients and timing for administering the assessments to the patients. The mechanisms generate a sequence of health care assessments, in the plurality of health care assessments, based on the guidelines and the patient information. The sequence comprises an ordering of the health care assessments, and a timing interval between health care assessments, determined based on the guidelines and the patient information. The mechanisms administer at least one health care assessment to the patient in accordance with the determined sequence of health care assessments.

U.S. Pat. No. 11,152,121 (Stoval, III, et al.) depicts a system for generating clinical summaries using machine learning. The computer system generates a clinical summary for a patient based on machine learning. One or more templates are generated, each indicating medical information for a corresponding clinical summary with respect to a medical condition of a patient. Preferences for medical information for each corresponding clinical summary are learned based on a history of desired medical information for clinical summaries for the medical condition. The learned preferences are applied to the one or more templates. A clinical summary is generated with respect to the medical condition of the patient based on the one or more templates with the learned preferences. Embodiments of the present invention further include a method and program product for generating a clinical summary for a patient based on machine learning in substantially the same manner described above.

The system of the present invention uses similar methods to improve the system artificial intelligence for future patients as each new patient is processed using care to safeguard the identity of each individual patient.

Throughout this application, various Patents and Applications are referenced by number and inventor. The disclosures of these documents in their entireties are hereby incorporated by reference into this specification in order to more fully describe the state of the art to which this invention pertains.

It is evident that many alternatives, modifications, and variations of the penicillin allergy test kit of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10—Allergy Test Kit
11—Container

12—Container QR Code
14—Preprinted Tattoo Label
15—Label QR Code
16—Sterile Alcohol Prep Pad
17—Sponge
18A—Multi-Site Skin Test System
18B—Multi-Site Skin Test System
20A—Multi-Site Skin Test Applicator
20B—Multi-Site Skin Test Applicator
21—Spine
25—Tester UP Indicator
30—Side Handle
31—Handle Grip
32—Handle Arm
34—Handle Leg
40A and 40B—Upward Scratching Barb
42A and 42B—Downward Scratching Barb
50—Fluid Tray
54—Reservoir
57—Allergy Test Fluid
60—Preloaded Syringe
62—Needle
64—Needle Hub Assembly
66—Safety Cover
72—Needle Shipping Position
74—Needle Insertion Position
76—Needle Disposal Position
90—Skin of Patient
91—Scratch
94—Raised Skin

We claim:

1. A kit for evaluating sensitivity to penicillin, said kit comprising:
   a. a container;
   b. a fluid tray having a plurality of fluid reservoirs, a first fluid reservoir for housing a first allergy test fluid, said first allergy test fluid being benzylpenicilloyl polylysine, a second fluid reservoir for housing a second allergy test fluid, said second allergy test fluid being penicillin G, said fluid tray being positionable within said container;
   c. a multi-site skin-test applicator for administering onto skin of a patient said first allergy test fluid and said second allergy test fluid, said multi-site skin-test applicator being in cooperative engagement with said fluid tray, a first piercing device generating a first piercing onto said skin at a first test site of said patient as said first allergy test fluid is deposited into said first piercing while a second piercing device generates a second piercing at a second test site onto said skin of said patient as said second allergy test fluid is deposited into said second piercing, said multi-site skin-test applicator being positionable within said container; and
   d. a first syringe being preloaded and a second syringe being preloaded, said first syringe and said second syringe being positionable within said container.

2. The kit of claim 1, further comprising a tattoo to be transferable onto said skin of said patient, said tattoo including a label, said label including a machine-readable code, said machine-readable code providing linkage to electronic medical records for said patient.

3. The kit of claim 1, wherein said multi-site skin-test applicator is a multiple scratch tester, said multiple scratch tester scratching said skin of said patient at said first test site depositing said first allergy test fluid, said multiple scratch tester scratching said skin of said patient at said second test site depositing said second allergy test fluid, a first scratching device generating a first scratch onto said skin of said patient as said first allergy test fluid is deposited into said first scratch while a second scratching device generates a second scratch onto said skin of said patient as said second allergy test fluid is deposited into said second scratch.

4. The kit of claim 1, wherein said first syringe is preloaded with benzylpenicilloyl polylysine.

5. The kit of claim 1, wherein said second syringe is preloaded with penicillin G.

6. The kit of claim 1, wherein said first syringe includes a safety syringe cover and a needle hub, a needle being secured in said needle hub, said needle being unused and locked in a first position and secured by said safety syringe cover during shipping; said needle being locked in a second position and secured by said safety syringe cover during insertion; and said needle being used and locked in a third position and secured by said safety syringe cover awaiting disposal.

7. A kit for evaluating a patient for sensitivity to penicillin, said kit comprising:
   a. a container;
   b. a fluid tray having a plurality of fluid reservoirs, a first fluid reservoir for housing a first allergy test fluid, said first allergy test fluid eliciting a cutaneous response in said patient after deposition if said patient is sensitive to penicillin, a second fluid reservoir for housing a second allergy test fluid, said fluid tray being positionable within said container;
   c. a multi-site skin-test applicator for administering onto skin of said patient said first allergy test fluid and said second allergy test fluid, said multi-site skin-test applicator being in cooperative engagement with said fluid tray, a first piercing device generating a first piercing onto said skin at a first test site of said patient as said first allergy test fluid is deposited into said first piercing while a second piercing device generates a second piercing at a second test site onto said skin of said patient as said second allergy test fluid is deposited into said second piercing, said multi-site skin-test applicator being positionable within said container; and
   d. a plurality of preloaded syringes, said plurality of preloaded syringes being positionable within said container, a first of said preloaded syringes being loaded with benzylpenicilloyl polylysine, and a second of said preloaded syringes being loaded with penicillin G.

8. The kit of claim 7, wherein said first allergy test fluid is benzylpenicilloyl polylysine.

9. The kit of claim 7, wherein said second allergy test fluid is penicillin G.

10. The kit of claim 7, further comprising a tattoo to be transferable onto said skin of said patient, said tattoo including a label, said label including a machine-readable code, said machine-readable code providing linkage to electronic medical records for said patient.

11. The kit of claim 7, wherein said multi-site skin-test applicator is a multiple scratch tester, said multiple scratch tester scratching said skin of said patient at said first test site depositing said first allergy test fluid, said multiple scratch tester scratching said skin of said patient at said second test site depositing said second allergy test fluid, a first scratching device generating a first scratch onto said skin of said patient as said first allergy test fluid is deposited into said first scratch while a second scratching device generates a second scratch onto said skin of said patient as said second allergy test fluid is deposited into said second scratch.

12. The kit of claim 7, wherein said first of said plurality of preloaded syringes includes a safety syringe cover and a needle hub, a needle being secured in said needle hub, said needle being unused and locked in a first position and secured by said safety syringe cover during shipping; said needle being locked in a second position and secured by said safety syringe cover during insertion; and said needle being used and locked in a third position and secured by said safety syringe cover awaiting disposal.

13. A kit for evaluating a patient for sensitivity to penicillin, said kit comprising:
   a. a container;
   b. a fluid tray having a plurality of fluid reservoirs, a first fluid reservoir for housing a first allergy test fluid, said first allergy test fluid eliciting a cutaneous response in said patient after deposition if said patient is sensitive to penicillin, a second fluid reservoir for housing a second allergy test fluid, said fluid tray being positionable within said container;
   c. a multi-site skin-test applicator for administering onto skin of said patient said first allergy test fluid and said second allergy test fluid, said multi-site skin-test applicator being in cooperative engagement with said fluid tray, a first piercing device generating a first piercing onto said skin at a first test site of said patient as said first allergy test fluid is deposited into said first piercing while a second piercing device generates a second piercing at a second test site onto said skin of said patient as said second allergy test fluid is deposited into said second piercing, said multi-site skin-test applicator being positionable within said container;
   d. a first preloaded syringe positionable within said container and a second preloaded syringe positionable within said container, wherein said first preloaded syringe is loaded with benzylpenicilloyl polylysine; and
   e. a tattoo that is transferable onto said skin of said patient, said tattoo including a label, said label including a tattoo digital identifier, said tattoo digital identifier being matchable with a computer app digital identifier thereby enabling matching patient electronic medical records with said kit, said tattoo being positionable within said container.

14. The kit of claim 13, wherein said first allergy test fluid is benzylpenicilloyl polylysine.

15. The kit of claim 13, wherein said second allergy test fluid is penicillin G.

16. The kit of claim 13, wherein said second preloaded syringe is loaded with penicillin G.

17. A kit for evaluating a patient for sensitivity to penicillin, said kit comprising:
   a. a container having a container digital identifier;
   b. a fluid tray having a plurality of fluid reservoirs, a first fluid reservoir for housing a first allergy test fluid, said first allergy test fluid eliciting a cutaneous response in said patient after deposition if said patient is sensitive to penicillin,
   a second fluid reservoir for housing a second allergy test fluid, said fluid tray being positionable within said container;
   c. a multi-site skin-test applicator for administering onto skin of said patient said first allergy test fluid and said second allergy test fluid, said multi-site skin-test applicator being in cooperative engagement with said fluid tray, a first piercing device generating a first piercing onto said skin at a first test site of said patient as said first allergy test fluid is deposited into said first piercing while a second piercing device generates a second piercing at a second test site onto said skin of said patient as said second allergy test fluid is deposited into said second piercing, said multi-site skin-test applicator being positionable within said container; and
   d. a first preloaded syringe positionable within said container and a second preloaded syringe positionable within said container, wherein said first preloaded syringe is loaded with benzylpenicilloyl polylysine.

18. The kit of claim 17, wherein said first allergy test fluid is benzylpenicilloyl polylysine.

19. The kit of claim 17, wherein said second allergy test fluid is penicillin G.

20. The kit of claim 17, wherein said second preloaded syringe is loaded with penicillin G.

* * * * *